(12) United States Patent
Kurata et al.

(10) Patent No.: US 6,443,931 B1
(45) Date of Patent: Sep. 3, 2002

(54) ABSORBENT ARTICLE FOR DISPOSAL OF BODY FLUIDS DISCHARGED THEREON

(75) Inventors: Nobuhiro Kurata; Mitsuhiro Wada, both of Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/488,911

(22) Filed: Jan. 21, 2000

(30) Foreign Application Priority Data

Jan. 21, 1999 (JP) .......................................... 11-012685

(51) Int. Cl.7 ................................................ A61F 13/20
(52) U.S. Cl. .................. 604/385.01; 604/370; 604/372; 604/384; 428/198
(58) Field of Search ......................... 604/385.01, 358, 604/370, 372; 428/198

(56) References Cited

U.S. PATENT DOCUMENTS 5,613,962 A * 3/1997 Kenmochi .................. 604/378
6,013,348 A * 1/2000 Takai ......................... 428/131

FOREIGN PATENT DOCUMENTS

WO      WO 9724095    * 7/1997 ........... A61F/13/15

* cited by examiner

*Primary Examiner*—Rodney M. Lindsey
*Assistant Examiner*—Angela J Grayson
(74) *Attorney, Agent, or Firm*—Baker & Daniels

(57) ABSTRACT

An absorbent article such as a panty liner for disposal of body fluids discharged thereon includes a body facing side, an undergarment facing side and an absorbent core disposed therebetween, the undergarment facing side including a thermoplastic synthetic fiber layer placed against a bottom surface of the core and having a density lower than that of the core, a synthetic resin layer having a density higher than that of the fiber layer and a first thermoplastic synthetic fiber having a density lower than that of the resin layer, and the synthetic fiber layer being coated with adhesive agent to an undergarment.

11 Claims, 2 Drawing Sheets

ABSORBENT ARTICLE FOR DISPOSAL OF BODY FLUIDS DISCHARGED THEREON

BACKGROUND OF THE INVENTION

This invention relates to an absorbent article for disposal of body fluids discharged thereon such as a sanitary napkin or a panty liner, particularly provided with fastening means by which the article is fastened to the wearer's clothes such as shorts.

In an absorbent article such as a sanitary napkin or a panty liner, it is well known to form its surface intended to contact the wearer's clothes (i.e., its surface intended to be kept free from contact with the wearer's skin) by plastic film and to coat the outer surface of the film with adhesive agent by means of which said article may be releasably fastened to the wearer's undergarment. It is also well known to replace the film by suitable breathable material such as a nonwoven fabric so that a breathability of the absorbent article may be improved and thereby stuffiness and/or skin eruption possibly produced during use of the article may be improved.

A film of olefine resin such as polyethylene has usually been used as the foregoing plastic film. Adhesive agent applied to the film of this type is apt to come off from the film unless the adhesive agent has a sufficient adhesive force. On the contrary, an excessively high adhesive force of the adhesive agent necessarily may result in an excessively high fastening force with which the panty liner is fastened to the undergarment. In an extreme case, it may be difficult to peel off the used panty liner from the undergarment. Even when the case is not so extreme, the panty liner once fastened to the undergarment will not be easily peeled off if it is desired to readjust a position at which the panty liner should be fastened to the undergarment.

Even if the film is replaced by a nonwoven fabric, there may occur an inconvenient situation that the adhesive agent applied on the nonwoven fabric transfers into the nonwoven fabric as time goes by until it becomes impossible to fasten the panty liner to the undergarment.

SUMMARY OF THE INVENTION

It is an object of this invention to provide an absorbent article for disposal of body fluids discharged thereon which is free from problems related to the adhesive agent.

According to this invention, there is provided an absorbent article for disposal of body fluids discharged thereon comprising a body facing side, an undergarment facing side and a liquid-absorbent core disposed therebetween, the undergarment facing side including at least a thermoplastic synthetic resin layer having a high density and placed against a bottom surface of the absorbent core and a first thermoplastic synthetic fiber layer having a density lower than that of the resin layer and bonded to a lower surface of the resin layer, and a lower surface of the first fiber layer being coated with adhesive agent to form a fastening zone to an undergarment.

According to one embodiment of this invention, the resin layer comprises a nonwoven fabric of thermoplastic synthetic fibers or plastic film.

According to another embodiment of this invention, the nonwoven fabric of thermoplastic synthetic fibers is a melt blown type nonwoven fabric.

According to still another embodiment of this invention, a second thermoplastic synthetic fiber layer having a density lower than that of the absorbent core is disposed between a bottom surface of the absorbent core and the resin layer.

According to further another embodiment of this invention, the resin layer, first fiber layer and second fiber layer are of breathable nature.

According to a further additional embodiment of this invention, the first fiber layer and second fiber layer are selected from a group consisting of a spun bond nonwoven fabric, a thermal bond nonwoven fabric, a spun lace nonwoven fabric and a laminate comprising two or more of these nonwoven fabrics.

According to still another additional embodiment of this invention, the second fiber layer has a basis weight of 30~150 g/m$^2$.

DETAILED DESCRIPTION OF THE PREFERRED EMBODIMENTS

Details of this invention will be more fully understood from the description of a panty liner as a specific example of an absorbent article for disposal of body fluids discharged thereon given hereunder with reference to the accompanying drawings.

Figure 1:
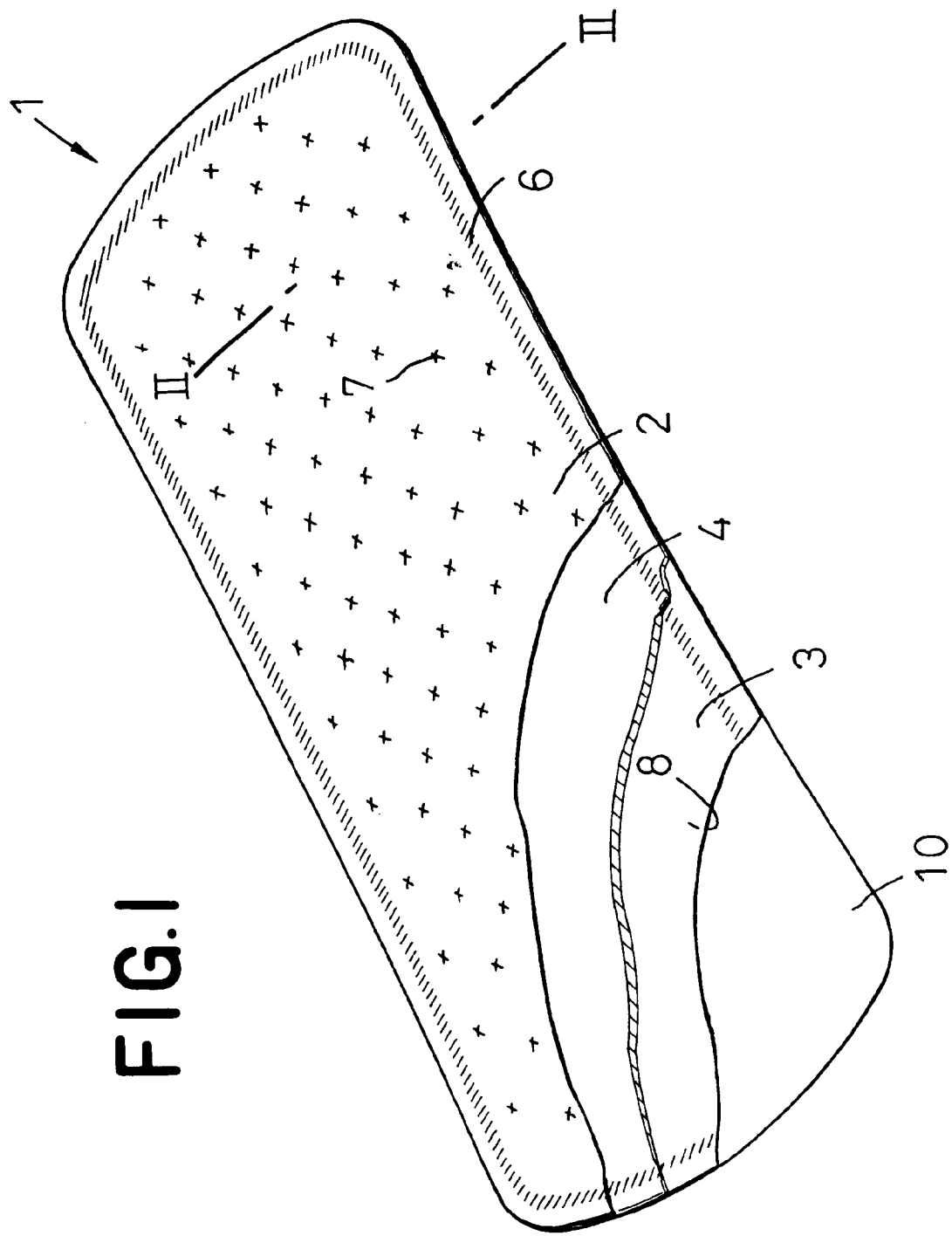
FIG. 1 is a perspective view showing a partially cutaway absorbent article (panty liner) according to this invention.

A panty liner 1 shown by FIG. 1 in a perspective view as partially broken away comprises a topsheet 2 defining a body facing surface, a backsheet 3 defining an undergarment facing surface and a liquid-absorbent core 4 disposed between these two sheets 2, 3. The topsheet 2 and backsheet 3 and the absorbent core 4 are identical one to another in shape as well as in size and bonded together along a pressure welding line 6 extending in parallel to a periphery of the liner 1. The topsheet 2 and the absorbent core 4 are bonded to each other also at a plurality of depressions 7 formed by embossing the topsheet 2 and absorbent core 4 from above the topsheet 2. A bottom surface 8 of the backsheet 3 is coated with adhesive agent 9 (See FIG. 2) to define a plurality of adhesive lines and the adhesive agent 9 is covered with a release paper 10 (See FIG. 2 also).

Figure 2:
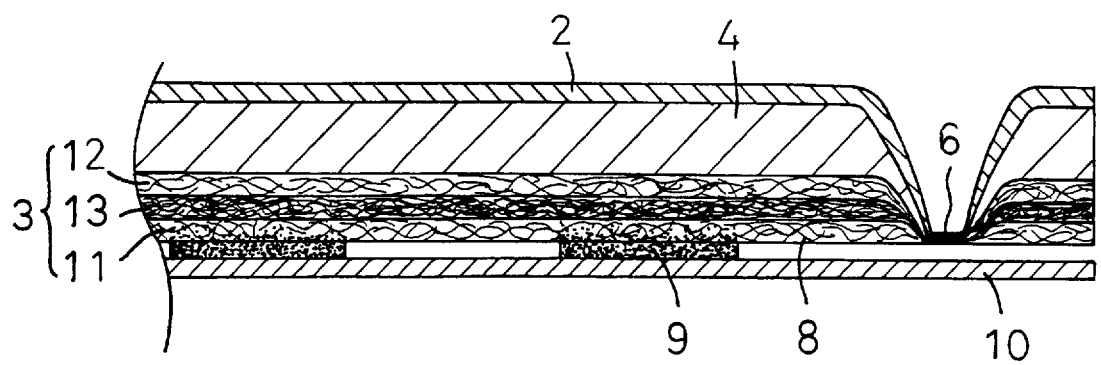
FIG. 2 is a fragmentary sectional view taken along a line II—II in FIG. 1.

FIG. 2 is a fragmentary sectional view taken along a line II—II in FIG. 1. A bottom surface of the topsheet 2 is closely in contact with the top surface of the absorbent core 4 so that the amount of body fluids discharged on the topsheet 2 may transfer to the absorbent core 4 as rapidly as possible. The backsheet 3 comprises an upper sheet 12 lying in contact with the bottom surface of the absorbent core 4, a lower sheet 11 intended to be placed in contact with a crotch region of undergarment and an intermediate sheet 13 disposed between the upper and lower sheets 12, 11. These sheets 11, 12, 13 are laminated one upon another and bonded together along the pressure welding line 6 or bonded together not only along the pressure welding line 6 but also at spots of hot melt adhesive agent or heat-sealing intermittently provided inside the pressure welding line 6.

The topsheet 2 is a liquid-pervious sheet made of a nonwoven fabric having a basis weight of 10~80 g/m$^2$ and containing 60% by weight or higher of hydrophilic fibers such as rayon fibers, pulp fiber or hydrophiled thermoplastic synthetic fibers.

The absorbent core 4 contains 100~60% by weight of rayon fibers, pulp fibers or hydrophiled thermoplastic synthetic fibers and 0~40% by weight of superabsorptive polymer particles so that the fibrous component may have a basis weight of 20~200 g/m² and a density of 0.08 g/cm³ or higher, more preferably of 0.15 g/cm³ or higher.

The upper sheet 12 making part of the backsheet 3 is made of a breathable nonwoven fabric of hydrophobic or water repellent thermoplastic synthetic fibers having a basis weight of 10~150 g/m² and a density lower than that of the absorbent core 4, preferably of 0.03~0.14 g/cm³. The lower sheet 11 is also made of a breathable nonwoven fabric of hydrophobic thermoplastic synthetic fibers having a basis weight of 10~40 g/m² and a density lower than that of the intermediate sheet 13, preferably of 0.05~0.14 g/cm³. The nonwoven fabric to be used as stock material for the upper and lower sheets 12, 11 may be selected from a group consisting of a spun bond nonwoven fabric, a thermal bond nonwoven fabric, a spun lace nonwoven fabric and a laminate comprising of two or more of these different type nonwoven fabrics. The intermediate sheet 13 is formed by a nonwoven fabric of hydrophobic thermoplastic synthetic fibers having a basis weight of 10~80 g/m², more preferably by a breathable melt blown nonwoven fabric having a basis weight of 10~80 g/m² and a density of 0.14 g/cm³ or higher or a breathable and hydrophobic thermoplastic synthetic resin film having a thickness of 0.01~0.08 mm. The outer surface of the lower sheet 11 is intermittently coated with the adhesive agent 9 so that a desired breathability of the lower sheet 11 may not be affected. While the adhesive agent 9 partially permeates fibrous interstices of the lower sheet 11 until it reaches the surface of the intermediate sheet 13, the high density intermediate sheet 13 prevents such permeation from easily going on beyond the surface of the intermediate sheet 13. The adhesive agent 9 is tangled with individual fibers of the lower sheet 11 and therefore reliably held by the liner 1 even if the adhesive agent 9 is of a relatively low adhesive force. In addition, it is not concerned that the adhesive agent 9 may be left on the undergarment in the course of stripping the liner 1 from the undergarment.

With the panty liner 1 arranged as has been described hereinabove, once an amount of body fluids has been absorbed held by the absorbent core 4, it is substantially ensured that the amount of body fluids does not easily transfer from the absorbent core 4 to the upper sheet 12 and further downward unless the wearer's body weight is exerted upon the absorbent core 4. This is for the reason that the bottom surface of the absorbent core 4 has a density lower than that of the absorbent core 4 itself and lined by the upper sheet 12 which is practically free from a capillary action. The upper sheet 12 serves as a barrier preventing the amount of body fluids from transferring downward and, particularly when the upper sheet 12 has a basis weight of 30~150 g/m², not only serves as such a barrier but also gives the panty liner 1 a high elastically restoring force against a compressive force exerted upon the panty liner 1 in the direction of its thickness. When the intermediate sheet 13 making part of the backsheet 3 is formed by a thermoplastic synthetic resin film, use of the upper sheet 12 can be eliminated because the film can serve as the barrier. All of the upper and lower sheets 12, 11 and the intermediate sheet 13 constituting the backsheet 3 are of breathable nature so that the backsheet 3 can prevent the amount of body fluids once having been absorbed by the absorbent core 4 from further transferring downward and thereby keep the bottom side of the liner 1 breathable.

While the invention has been described hereinabove taking the panty liner 1 as a specific example, it should be understood that this invention is applicable, in addition to the panty liner 1, the other various absorbent articles for disposal of body fluids discharged thereon such as a sanitary napkin, a urine-absorbent pad for incontinent user and a disposable diaper. These articles will be suitable for disposal of a relatively small amount of body fluids as in the case of the panty liner 1 so far as the intermediate sheet 13 of the backsheet 3 is formed by a nonwoven fabric of thermoplastic synthetic fibers. On the other hand, these article will be suitable for disposal of a relatively large amount of body fluids as in the case of the sanitary napkin or the disposable diaper so far as the intermediate sheet 13 is formed by a thermoplastic synthetic resin film.

As will be apparent from the foregoing description, the backsheet in the absorbent article for disposal of body fluids discharged thereon at least comprises the thermoplastic synthetic resin layer having a relatively high density and the thermoplastic synthetic fiber layer underlying the thermoplastic synthetic resin layer and having a relatively low density. The adhesive agent serving as fastening means by which the article is fastened to the undergarment is tangled with individual fibers of the synthetic fiber layer and thereby reliably held on the bottom surface of the article. In addition, the adhesive agent is prevented by the resin layer from transferring into the backsheet. With the arrangement in which the backsheet includes the thermoplastic synthetic fiber layer having a density lower than that of the absorbent core disposed between the bottom surface of the absorbent core and the resin layer, the amount of body fluids once having been held by the absorbent core is prevented from further transferring toward the backsheet. The backsheet may be formed by breathable stock material to improve the breathability of the absorbent article.

What is claimed is:

1. An absorbent article for receiving and containing body fluids discharged thereon comprising:
   a body facing side;
   an undergarment facing side; and
   a liquid-absorbent core disposed between the body facing side and the undergarment facing side,
   said undergarment facing side including:
      a first nonwoven, non-apertured fabric layer of thermoplastic synthetic fibers placed against a bottom surface of said liquid-absorbent core; and
      a second nonwoven non-apertured layer of thermoplastic synthetic fibers having a density lower tan a density of said first nonwoven fabric layer, and bonded to a lower surface of said first nonwoven fabric layer,
      a lower surface of said second nonwoven fiber layer being coated with adhesive agent for fastening said absorbent article to an undergarment.

2. An absorbent article according to claim 1, wherein said second nonwoven fabric of thermoplastic synthetic fibers comprises a melt blown nonwoven fabric.

3. An absorbent article according to claim 1, wherein a third nonwoven fabric layer of thermoplastic synthetic fibers having a density lower than a density of said liquid-absorbent core is disposed between the bottom surface of said liquid-absorbent core and said first nonwoven fabric layer.

4. An absorbent article according to claim 1, wherein said first nonwoven fabric layer comprises a melt blown nonwoven fabric.

5. An absorbent article according to claim 4, wherein said first, second and third nonwoven fabric layers each have breathable properties.

6. An absorbent article according to claim 4, wherein said first, second and third nonwoven fabric layers are selected from the group consisting of a spun bond nonwoven fabric, a thermal bond nonwoven fabric, a spun lace nonwoven fabric and a laminate comprising two or more of these nonwoven fabrics.

7. An absorbent article according to claim 4, wherein said third nonwoven fabric layer has a basis weight of 30–150 g/m$^2$.

8. An absorbent article for receiving and containing body fluids discharged thereon comprising:

a body facing side;

an undergarment facing side; and a liquid-absorbent core disposed between the body facing side and the undergarment facing side, said undergarment facing side including:

a breathable, non-apertured film layer of thermoplastic synthetic resin placed against a bottom surface of said liquid-absorbent core, and a first breathable nonwoven, non-apertured fabric layer of thermoplastic synthetic fibers having a density lower than a density of said film layer and bonded to a lower surface of said breathable film layers, and a lower surface of said first breathable nonwoven fabric layer being coated with adhesive for fastening said absorbent article to an undergarment.

9. An absorbent article according to claim 8, wherein a breathable second nonwoven fabric layer of thermoplastic synthetic fibers having a density lower than a density of said liquid-absorbent core disposed between the bottom surface of said liquid-absorbent core and said first nonwoven fabric layer.

10. An absorbent article according to claim 8, wherein said first and second breathable nonwoven fabric layers are selected from the group consisting of a spun bond nonwoven fabric, a thermal bond nonwoven fabric, a spun lace nonwoven fabric and a laminate comprising two or more of these nonwoven fabrics.

11. An absorbent article according to claim 8, wherein said second breathable nonwoven fabric layer has a basis weight of 30–150 g/m$^2$.

* * * * *